US012748063B2

(12) United States Patent
Chen et al.

(10) Patent No.: US 12,748,063 B2
(45) Date of Patent: Sep. 29, 2026

(54) METHOD FOR SOURCE ROCK MATURITY DETERMINATION USING STATIC HIGH-FIELD NUCLEAR MAGNETIC RESONANCE SPECTROSCOPY

(71) Applicant: Saudi Arabian Oil Company, Dhahran (SA)

(72) Inventors: Jin-Hong Chen, Katy, TX (US); Stacey Marie Althaus, Houston, TX (US); David Jacobi, The Woodlands, TX (US); Mohammed Boudjatit, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 159 days.

(21) Appl. No.: 18/738,336

(22) Filed: Jun. 10, 2024

(65) Prior Publication Data

US 2025/0377320 A1 Dec. 11, 2025

(51) Int. Cl.

| | |
|---|---|
| ***G01V 3/00*** | (2006.01) |
| ***G01N 24/08*** | (2006.01) |
| ***G01N 33/24*** | (2006.01) |
| ***G01R 33/46*** | (2006.01) |

(52) U.S. Cl.

CPC ......... *G01N 24/081* (2013.01); *G01N 33/241* (2013.01); *G01R 33/4625* (2013.01)

(58) Field of Classification Search

CPC . G01N 24/081; G01N 33/241; G01R 33/4625
USPC .......................................................... 324/309
See application file for complete search history.

(56) References Cited

U.S. PATENT DOCUMENTS

| | | | | |
|---|---|---|---|---|
| 9,176,081 B2 | 11/2015 | Sen et al. | | |
| 10,360,282 B2 | 7/2019 | Rasmus et al. | | |
| 10,760,418 B1 * | 9/2020 | Liu | G01N 1/08 | |
| 2014/0084927 A1 * | 3/2014 | Walsh | G01V 3/14 | 324/322 |

FOREIGN PATENT DOCUMENTS

| | | | |
|---|---|---|---|
| CN | 211927499 U * | 11/2020 | |
| CN | 112014345 A * | 12/2020 | G16C 20/70 |
| CN | 113176289 A * | 7/2021 | G01N 25/00 |
| CN | 111551652 B * | 4/2022 | G01N 30/02 |
| EP | 3224604 B1 * | 8/2019 | E21B 49/00 |

(Continued)

OTHER PUBLICATIONS

Clough et al., "Characterization of Kerogen and Source Rock Maturation Using Solid-State NMR Spectroscopy," Energy & Fuels, 2015, 29(10):6370-6382, 42 pages.

(Continued)

*Primary Examiner* — Walter L Lindsay, Jr.
*Assistant Examiner* — Frederick Wenderoth
(74) *Attorney, Agent, or Firm* — Fish & Richardson P.C.

(57) ABSTRACT

A system and method for measuring a source rock sample's maturity by a static high field resolution nuclear magnetic resonance (NMR) spectroscopy is disclosed. Kerogen, a part of the source rock matrix is studied, to quantify the amount of hydrogen (H) and carbon (C) present. This technique is non-destructive and non-invasive to the sample. The method further includes determining the H/C ratio of the kerogen in the source rock sample by integrating the H/C ratio of a known external reference sample.

19 Claims, 4 Drawing Sheets

(56) References Cited

FOREIGN PATENT DOCUMENTS

| | | | | |
|---|---|---|---|---|
| WO | WO-2014006592 A2 * | 1/2014 | ............... | G01V 3/06 |
| WO | WO 2022159542 A1 | 7/2022 | | |

OTHER PUBLICATIONS

Diessel et al., "Coalification and graphitization in high-pressure schists in New Caledonia," Contributions to Mineralogy and Petrology, 1978, 68(1):63-78, 16 pages.
Dow, "Kerogen Studies and Geological Interpretations," Journal of Geochemical Exploration, 1977, 7:77-97, 21 pages.
Mo et al., "Solvent Signal as an NMR Concentration Reference," Analytical Chemistry, 2008, 80(24):9835-9839, 5 pages.
Peters, "Guidelines for evaluating petroleum source rock using programmed pyrolysis," AAPG Bulletin, Mar. 1986, 70:318-329, 13 pages.

* cited by examiner

METHOD FOR SOURCE ROCK MATURITY DETERMINATION USING STATIC HIGH-FIELD NUCLEAR MAGNETIC RESONANCE SPECTROSCOPY

TECHNICAL FIELD

This disclosure relates to methods of determining source rock maturity using static high field nuclear magnetic resonance (NMR) spectroscopy.

BACKGROUND

Source rocks are fine-grained, organic-rich mud rocks with extremely low permeability in the micro-to nano-Darcy range. They contain organic matter, predominantly kerogen, which is intertwined within the mineral matrix. Thermal maturity is one of the most important parameters that measures the transformation of a source rock into hydrocarbons as a function of temperature and time. Several ways have been devised to measure maturity of source rocks. The most commonly applied methods are vitrinite reflectance and pyrolysis measurement. However, each of these methods has disadvantages.

The vitrinite reflectance method determines thermal maturity microscopically, using visual-light and reflectance intensities recorded from vitrinite macerals in polished rock surfaces immersed in oil. This technique is labor intensive, prone to subjective interpretation of the intensities measured, and is subject to human errors caused by the difficulty in microscopically distinguishing vitrinite from the other two groups of macerals that also compose kerogen: liptinites and inertinites. As a result, it is often challenging to assess maturity in source rocks using this technique.

Pyrolysis involves heating a powdered source rock sample in an oven according to a programmed temperature ramp. This causes the sample to decompose thermally. The maturity-based properties of the rock are revealed according to a "pyrogram," which is a visual graph of its thermal decomposition as a function of time and temperature, as detected and measured from a flame ionization detector. However, in this method the original sample is destroyed during the process. Additionally, over-mature samples possess very broad signals that possess no definable apex, causing uncertainty over the true value.

The vitrinite reflectance method and pyrolysis method are seeking to measure kerogen hydrocarbon volatility. As a source rock matures and generates hydrocarbons, hydrogen is lost relative to carbon, such that a decreasing H/C ratio can be used to track the progression of the loss of volatility. With this loss, the aromaticity of the kerogen also increases which can be measured using Solid State Nuclear Magnetic Resonance using a technique called magic angle spinning (Clough et al., Energy and Fuels, 2015, v.29, No. 10, p. 6370-6382).

However, these measurements are made on kerogen that has been segregated from the rock, requiring the acid digestion of the rock sample to recover the kerogen. During the digestion process, secondary mineralization can occur that can influence the values obtained. As a result of this challenge, as well as the other issues associated with pyrolysis and vitrinite reflectance, all of which require the destruction of the sample, a non-destructive method to determine maturity would be advantageous so that other measurements could be made on the intact sample.

SUMMARY

An embodiment described here provides a method for measuring a source rock's maturity using static high field nuclear magnetic resonance (NMR) spectroscopy. Kerogen, a part of the source rock matrix is studied, to quantify the amount of hydrogen and carbon present. This technique addresses the challenge of sample destruction, by using a non-destructive and non-invasive, static high-resolution nuclear magnetic resonance (NMR) spectroscopy. This method directly measures the quantities of hydrogen and carbon of kerogen in a source rock sample, comparable to elemental analysis to determine the maturity of the source rock. The sample can be an intact small core plug or crushed rocks.

Provided in the present disclosure is a method for analyzing maturity of a subterranean hydrocarbon rock, the method including obtaining a subterranean hydrocarbon rock sample by drilling through a subterranean zone; extracting bitumen out of the subterranean hydrocarbon rock sample using a solvent; placing the subterranean hydrocarbon rock sample in a nuclear magnetic resonance (NMR) tube; and measuring a $^{1}H$ spectrum and a $^{13}C$ NMR spectrum with a NMR probe using an NMR spectrometer comprising a static state high resolution measurement technique.

In some embodiments of the method, the subterranean hydrocarbon rock sample has micro to nano Darcy permeability.

In some embodiments of the method, the subterranean hydrocarbon rock sample includes a kerogen intertwined within a mineral matrix. In some embodiments, the method further includes measuring a hydrogen and carbon (H/C) ratio of the kerogen. In some embodiments, measuring the H/C ratio includes measuring a degree of aromaticity of the kerogen for the subterranean hydrocarbon rock sample.

In some embodiments of the method, measuring the $^{1}H$ spectrum and the $^{13}C$ NMR spectrum is performed on an intact subterranean hydrocarbon rock sample without further treatment.

In some embodiments, the method further includes measuring the $^{1}H$ spectrum and the $^{13}C$ NMR spectrum of the NMR tube and the NMR probe as a background signal, where the background signal is subtracted from the $^{1}H$ spectrum and the $^{13}C$ NMR spectrum of the subterranean hydrocarbon rock.

In some embodiments, the method further includes measuring the H/C ratio of kerogen in the subterranean hydrocarbon rock sample by integrating the H/C ratio of an external reference pure organic sample. In some embodiments, the external reference sample is benzene, hexane, or dimethylpolysiloxane.

Also provided in the present disclosure is a system for measuring maturity of a subterranean rock, the system including a nuclear magnetic resonance (NMR) spectrometer containing an NMR probe, where the NMR is configured to operate with a static high resolution technique; a sample tube, where a subterranean rock sample is placed; and a user display system to represent an output NMR spectra comprising a $^{1}H$ spectrum and a $^{13}C$ NMR spectrum.

In some embodiments of the system, the subterranean rock includes a kerogen intertwined within a mineral matrix. In some embodiments, a hydrogen/carbon (H/C) ratio of the kerogen is measured by the NMR spectrometer as the $^{1}H$ spectrum and the $^{13}C$ NMR spectrum. In some embodiments, the NMR spectrometer includes a measurement of the $^{1}H$ spectrum and the $^{13}C$ NMR spectrum of the NMR probe and the sample tube as a background signal.

In some embodiments of the system, the subterranean rock sample includes small core plugs or crushed rocks.

In some embodiments, the system further includes a user defined temperature setting for the NMR spectrometer.

Also provided in the present disclosure is a method of analyzing subterranean rock, the method including obtaining a subterranean rock sample as a core plug or crushed rock; placing the subterranean rock sample in a sample tube; performing a static state high resolution nuclear magnetic resonance (NMR) spectroscopic measurement with a NMR probe to obtain a $^{1}H$ spectrum and a $^{13}C$ NMR spectrum; and displaying the $^{1}H$ spectrum and the $^{13}C$ NMR spectrum on a user display system.

In some embodiments of the method, the subterranean rock sample contains an organic-rich shale or mudrock.

In some embodiments of the method, the subterranean rock sample comprises a kerogen intertwined within a mineral matrix. In some embodiments, a hydrogen/carbon (H/C) ratio of the kerogen is measured by the NMR spectroscopic measurement. In some embodiments, the method further includes measuring the H/C ratio of kerogen by integrating the H/C ratio of an external reference sample, where the external reference sample is dimethylpolysiloxane.

DETAILED DESCRIPTION

Figure 1:
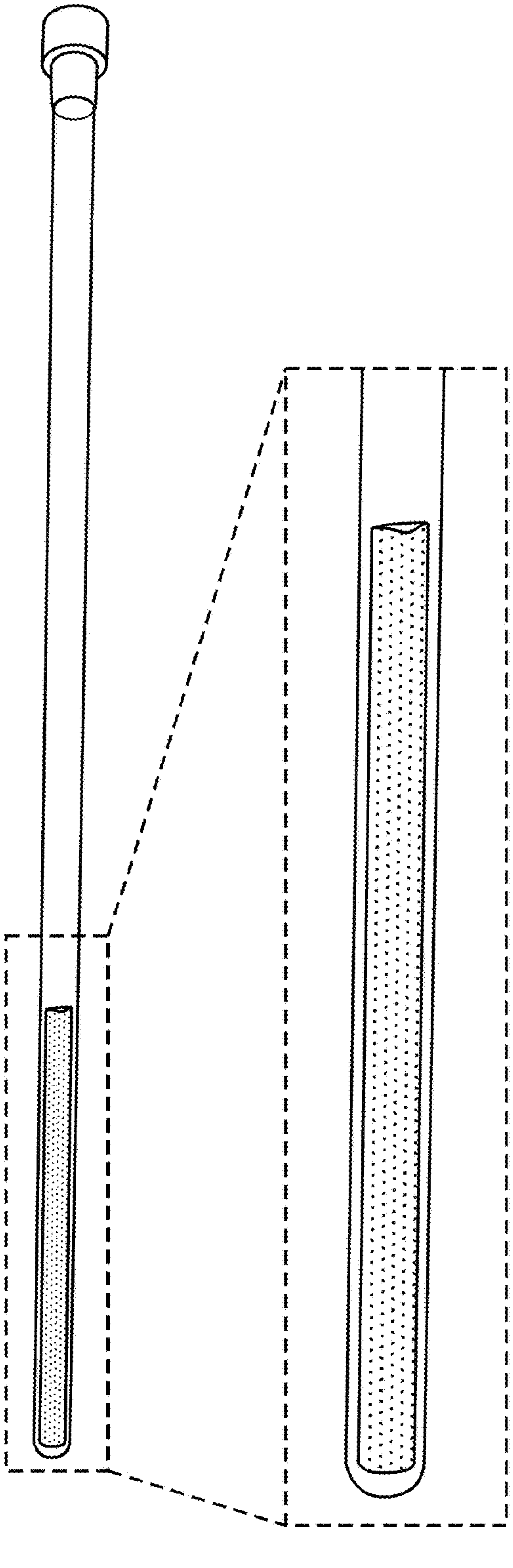
FIG. 1 is a drawing of a core plug sample in a NMR sample tube.

Source rocks are rocks that have the potential to generate oil and natural gas and are essential for the commercial accumulation of oil and gas. Source rocks are commonly shales and lime mudstones. Studies on the thermal maturity of source rocks are critical to estimate organic richness, geochemistry characteristics, hydrocarbon type, and if the proper kerogen type is present. This information is vital to assess prospective oil and gas plays and drilling locations. For example, the more mature the source rock, the more favorable the conditions for hydrocarbon generation.

Embodiments described herein provide a system for analyzing source rock maturity from a subterranean formation, using static high resolution nuclear magnetic resonance (NMR) spectroscopy. NMR is a widely used analytical method that can determine the quantity and structure of a material. In earlier measurements, kerogen a part of the rock matrix, was investigated by solid-state NMR technology by spinning the sample at a high rate to remove the dipolar coupling. However, the molecules comprising the kerogen are mobile enough that the typical spectral linewidth from $^{1}H$-$^{1}H$ dipolar coupling is about 14 kHz (Chen J. H. et all, paper-022, 2023 SCA Symposium, Oct. 9-12, 2023, Abu Dhabi, UAE). The static spectrum of kerogen thus can be easily acquired using a pulse with length of 10 μs which can excite a frequency bandwidth of about 160 kHz. The linewidth of $^{13}C$ spectrum due to $^{1}H$-$^{13}C$ dipolar coupling is only about 25% of the $^{1}H$-$^{1}H$ dipolar coupling and thus in the range of 3.5 kHz and can also easily be acquired. Therefore, $^{1}H$ and $^{13}C$ NMR spectra can be acquired at a static state. Consequently, the hydrogen/carbon (H/C) ratio of the source rock shale sample is determined.

An aspect described herein provides a method of measuring the $^{1}H$ and $^{13}C$ spectra for a subterranean source rock sample. The methods of the present disclosure are non-destructive to the source rock sample. The source rock sample can be a core plug or a crushed rock. In implementations herein, bitumen from the source rock is extracted using a solvent. In some embodiments, the solvent includes aromatic hydrocarbons, cyclic hydrocarbons, organochlorine compounds, alcohols, or a mixture of alcohols and aromatic compounds. In some implementations herein, toluene, hexane, cyclohexane, benzene, chloroform, or dichloromethane are used as the solvents. In some embodiments, after extracting bitumen, the source rock sample is placed in a NMR sample tube. In some embodiments, the NMR sample tube is placed inside the NMR spectrometer. The spectrometer is set at a user-defined temperature and the sample tube is heated to match the user-defined temperature. The $^{1}H$ and $^{13}C$ NMR spectra for the NMR sample tube and the NMR probe is deducted from the $^{1}H$ and $^{13}C$ NMR spectra of the source rock sample (after extraction of bitumen). Integration of the $^{1}H$ and $^{13}C$ NMR spectra of the source rock sample gives the total amount of hydrogen and carbon in the sample.

An aspect described herein provides a method of determining the total hydrogen and carbon in the source rock sample containing kerogen. The NMR method uses an internal or an external reference, for example, by adding a known amount of a chemical with a simple $^{1}H$ and $^{13}C$ spectrum. In some implementations herein, the reference compound is dimethylpolysiloxane (DMPS). DMPS contains α mole of $^{1}H$ and β mole of $^{13}C$. The hydrogen and carbon content for DMPS can be obtained from literature, from the molecular structure, or independently measured. The acquired DMPS $^{1}H$ and $^{13}C$ NMR spectra are integrated to give total hydrogen and carbon in the reference DMPS. The ratio of the hydrogen to carbon in the source rock sample is obtained using the integrated spectra of the source rock sample, the reference sample, and the molar ratio α/β of hydrogen and carbon in the reference sample.

The method of the present disclosure addresses the challenge of sample destruction, by using non-destructive and non-invasive, static high-resolution nuclear magnetic resonance (NMR) spectroscopy. This method directly measures the quantities of hydrogen and carbon of kerogen in a source rock sample, comparable to elemental analysis, to determine the maturity of the source rock. The sample can be an intact small core plug or crushed rocks.

The details of one or more implementations are set forth in the accompanying drawings and the description below. Other features and advantages will become apparent from the description, drawings, and the claims.

FIG. 1 is a drawing of a core plug sample in a NMR sample tube. A core plug is obtained by drilling through a subterranean zone. The core drilling process is an expensive process and often limited in size. A block of source rock from the subterranean zone is drilled out. Uniform cylindrical core samples, called core plugs, from the same block are drilled and used for NMR spectra analysis. The source rocks are organic-rich shale with very low permeability, for example, in the micro to nano Darcy range. In some implementations, the sample core plugs are crushed and measurements are performed on a crushed sample. In some implementations, the core plug undergoes a treatment procedure to remove certain organic material for NMR analysis such as pore space measurement, where a single fluid is preferred. The NMR analysis can measure other source rock properties such as total organic content, oil and water saturation, wettability, porosity, or hydraulic conductivity.

In some implementations, the core plug sample, crushed core plugs, or crushed rock samples do not have to undergo any cleaning procedure. The intact sample as obtained is used for studying the organic content in the source rock. Organic content in the source rock is divided into two categories based on its solubility in an organic solvent. Bitumen is soluble in organic solvents, whereas other organic matter such as kerogen is not soluble in organic solvents. Kerogen is the most abundant organic matter which is intertwined with the mineral matrix. Kerogen is a solid, insoluble, and non-volatile organic matter. The molecular structure includes complex hydrocarbons with varying amounts of nitrogen, sulfur, and oxygen. The molecular structure controls the type, amount, and quality of hydrocarbons formed during thermal maturation. Kerogens are classified as Type I to Type IV. Type I kerogen comes from a marine environment and has a higher aliphatic content. Type III kerogen is obtained from terrestrial organic material and contains a higher proportion of aromatic compounds. Type II kerogen is intermediate and contains both aliphatic and aromatic compounds. Type II kerogen may be obtained from marine or terrestrial sources. Type IV kerogen includes mostly inert organic matter in the form of polycyclic aromatic compounds. They have negligible potential to generate hydrocarbons. One of the most important features for the generation of oil and gas is the maturity level of the source rock. Organic matter has to reach a certain maturity before thermal degradation can occur, resulting in the formation of liquid and gaseous hydrocarbons. The determination of source rock maturity is critical to the success of oil exploration programs.

In some implementations, the bitumen is extracted from the core plug sample using a solvent. This extraction is done to remove the NMR signals from the bitumen, which also contributes to the $^{1}H$ and $^{13}C$ NMR signal. In some implementations, the solvent includes aromatic hydrocarbons, cyclic hydrocarbons, organochlorine compounds, alcohols, or a mixture of alcohols and aromatic compounds. In some implementations herein, toluene, cyclohexane, or dichloromethane are used as the solvents. The core plug or crushed rock sample is placed in a sample tube made of glass. The diameter of the sample tubes can vary based on the core plug or rock sample size.

Various NMR methods including imaging, relaxation, and diffusion are non-invasive methods to study the structure and geological properties of a rock sample. The NMR resonance frequencies depend on the nuclei of the molecules in the sample. It is possible to identify the chemical compositions of the molecules based on the difference in the resonance frequencies when an external magnetic field is applied. A strong magnetic field with a high level of homogeneity is desirable for strong resolution in the NMR studies.

Figure 2:
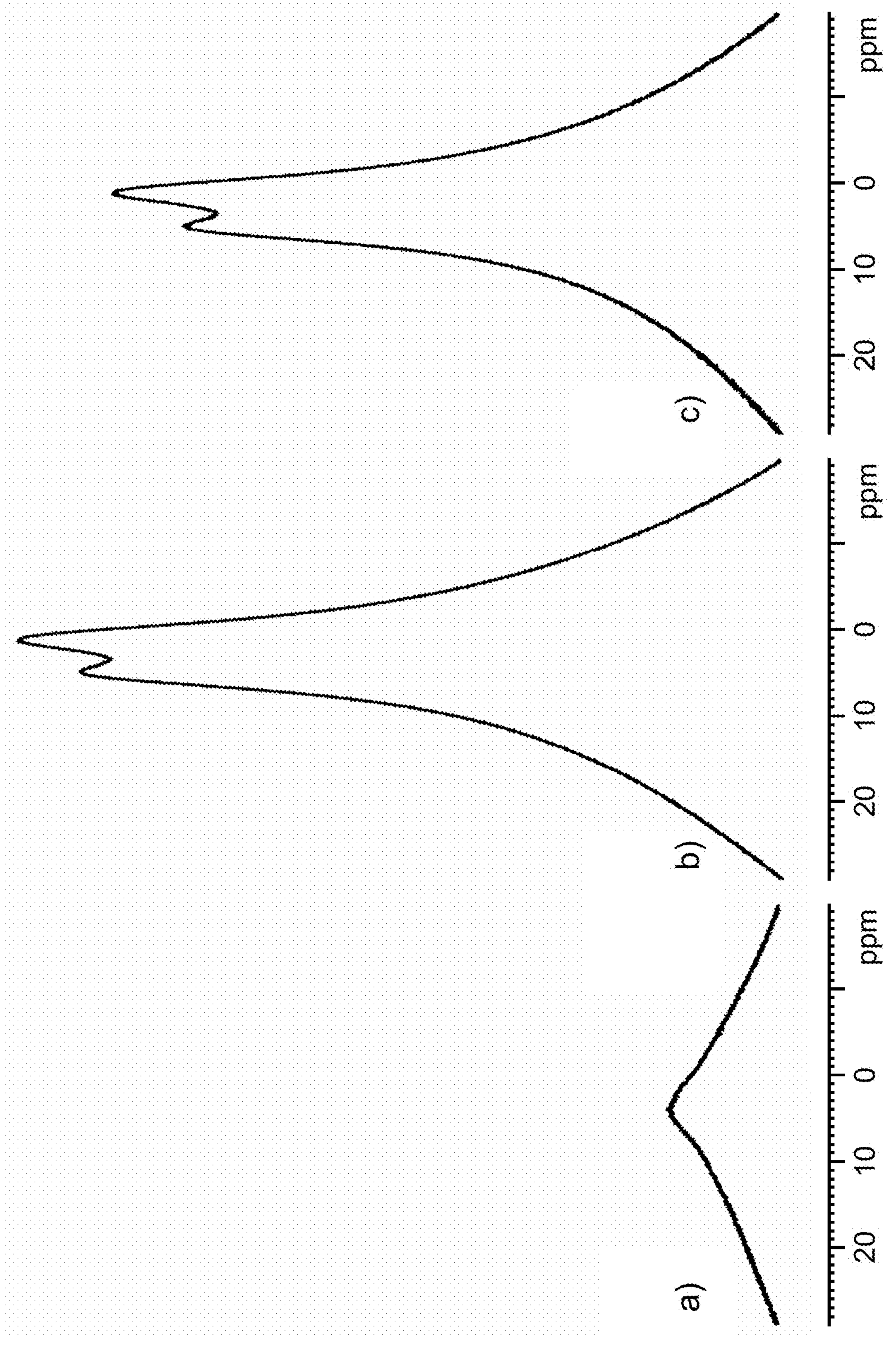
FIG. 2 is a $^{1}H$ NMR spectra representation of a source rock sample.

FIG. 2 is a $^{1}H$ NMR spectra representation of a source rock sample. In some implementations, the source rock sample includes a core plug or a crushed rock sample. The source rock, after being placed in the NMR sample tube, is heated to a user defined temperature set on the NMR system. Upon reaching the set temperature, the NMR measurements are performed. The $^{1}H$ and $^{13}C$ spectra are first performed on the sample tube and the NMR probe. The tube and the NMR probe have a background $^{1}H$ and $^{13}C$ signal which are labelled as Shd bg$^{1H}$ and $S_{bg}{}^{13C}$. The $^{13}C$ background NMR signal in most scenarios is negligible but, in some cases, the sample tube and/or probe could contain nonnegligible $^{13}C$ NMR signal.

The sample tube is taken out and the source rock sample is placed in it. The same NMR acquisition parameters such as temperature, frequency, and time are set as in the previous step. The $^{1}H$ and $^{13}C$ spectra are obtained for the source rock sample. It can be expressed as $S_{sum}{}^{1H}$ and $S_{sum}{}^{13C}$, respectively. The spectra also include the background signal. The background signal can be subtracted from the sample signal to obtain the spectra for the source rock sample. This is expressed as:

$$S_{rock}^{1H} = S_{sum}^{1H} - S_{bg}^{1H}$$

$$S_{rock}^{13C} = S_{sum}^{13C} - S_{bg}^{13C}$$

In FIG. 2, spectra a) represents the background signal $S_{bg}{}^{1H}$ obtained from the sample tube and the NMR probe. The spectra b) represents the total spectra $S_{sum}{}^{1H}$ obtained. This includes the background signal and the signal from the source rock sample. The spectra c) is the $S_{rock}{}^{1H}$ signal obtained after the subtraction of the background signal.

Figure 3:
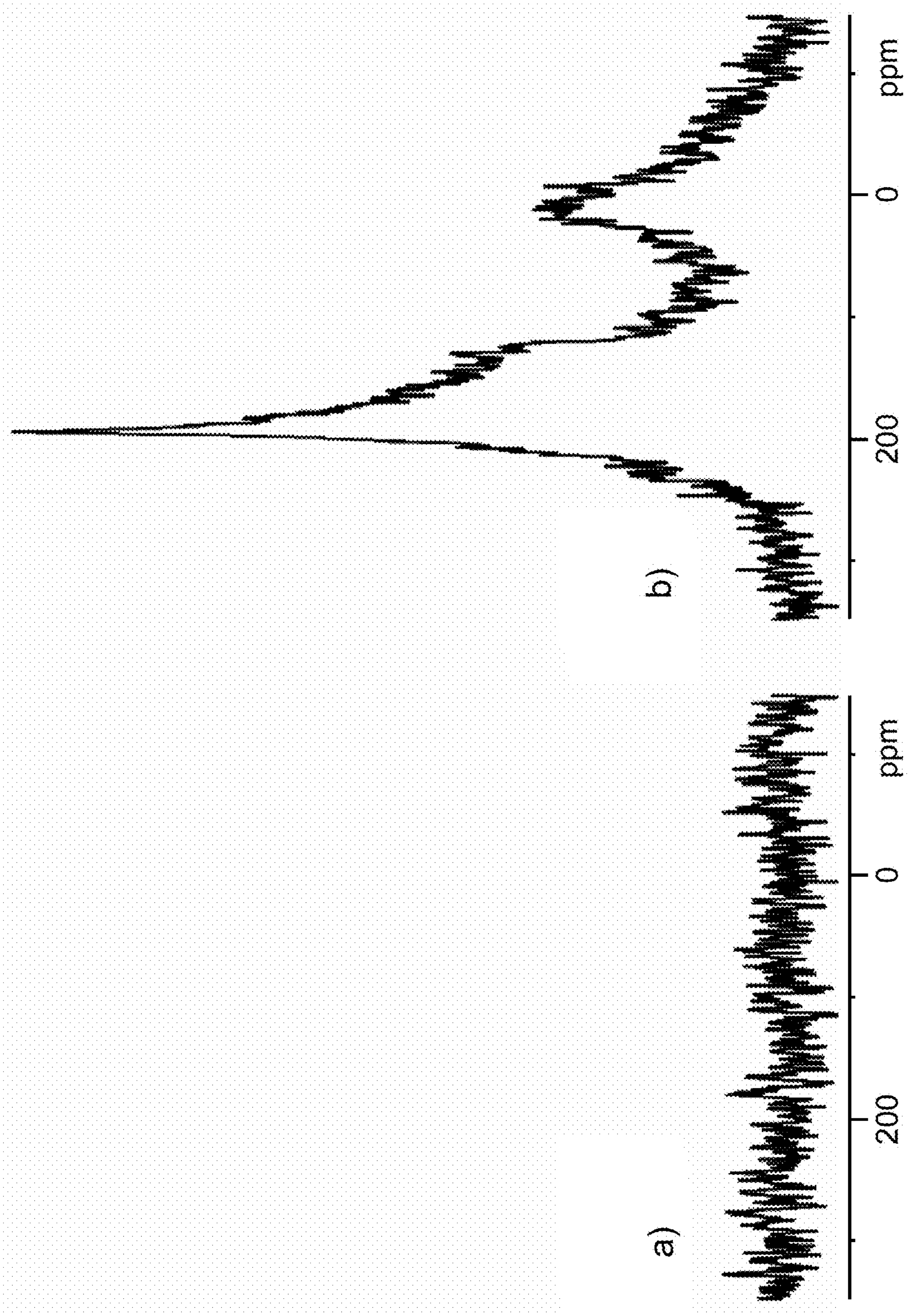
FIG. 3 is a $^{13}C$ NMR spectra representation of a source rock sample.

FIG. 3 is a $^{13}C$ NMR spectra representation of a source rock sample. In some implementations, the background signal $S_{bg}{}^{13C}$ is negligible as observed in FIG. 3, spectra a). In this case $S_{rock}{}^{13C}=S_{sum}{}^{13C}$. Spectra b) shows the total $^{13}C$ spectra for the source rock sample.

Integration of the acquired $^{1}H$ and $^{13}C$ spectra for the source rock sample gives the total amount of hydrogen and carbon in the sample expressed as $I_{rock}{}^{1H}$ and $I_{rock}{}^{13C}$, respectively. Quantification of the total hydrogen and carbon in the source rock sample is done using the routine NMR method using an external reference, e.g., by adding a known amount of chemical with a simple $^{1}H$ and $^{13}C$ spectrum. The external reference samples include pure organic solvents. In some implementations, the chemical used as a reference is dimethylpolysiloxane (DMPS), benzene, or hexane. In implementations here, DMPS as a reference chemical contains α mole of $^{1}H$ and β mole of $^{13}C$, which can be obtained from the molecular structure or measured independently. The acquired DMPS $^{1}H$ and $^{13}C$ NMR signals are integrated to give $I_{ref}{}^{1H}$ and $I_{ref}{}^{13C}$, respectively. The ratio R of hydrogen and carbon in the source rock sample is then obtained using the below expression:

$$R = \frac{I_{rock}^{1H} / I_{ref}^{1H}}{I_{rock}^{13C} / I_{ref}^{13C}} * \frac{\alpha}{\beta}$$

Figure 4:
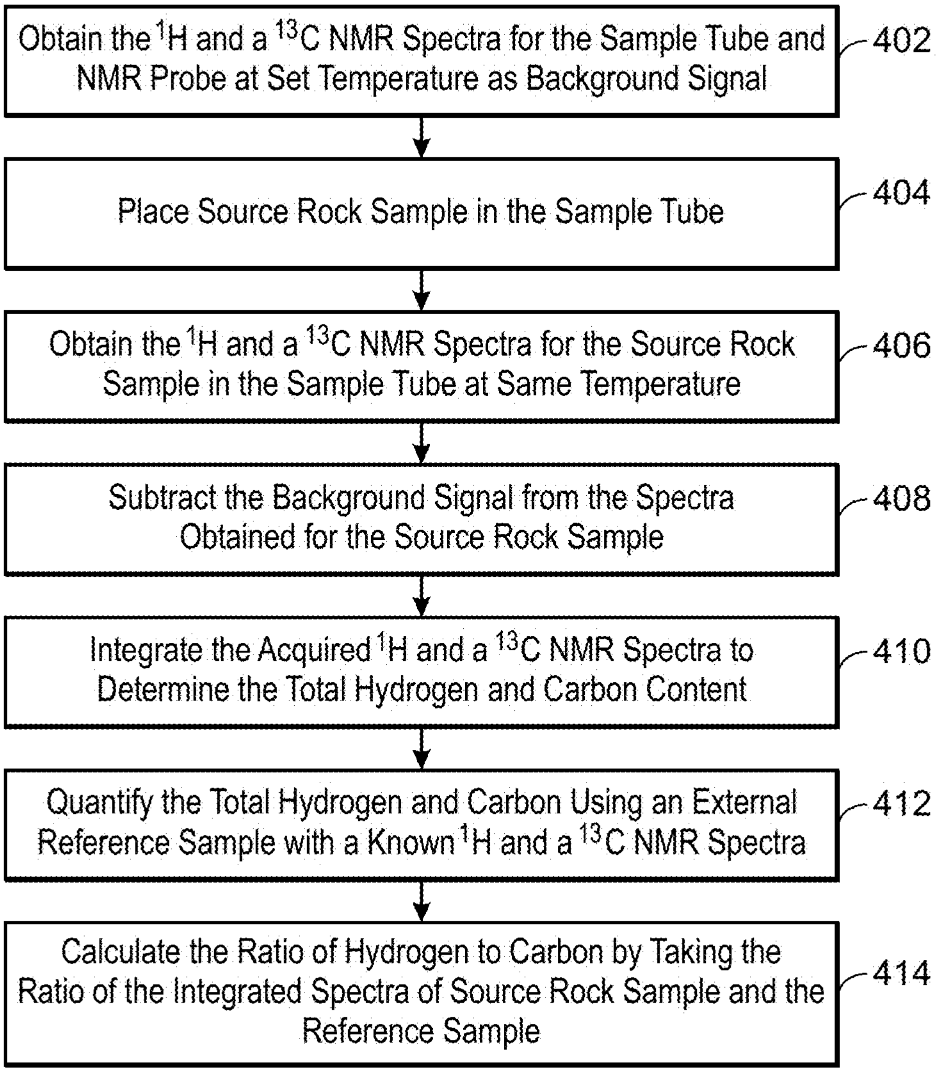
FIG. 4 is a flow diagram of the sequence of steps in obtaining the H/C ration for the source rock sample.

FIG. 4 is a flow diagram of the sequence of steps in obtaining the H/C ratio for the source rock sample. The H/C ratio in the kerogen present in the source rock sample is used to determine thermal maturity, which can be studied using NMR. A decreasing H/C ratio of kerogens indicates higher maturity, indicating increased hydrocarbon formation. Kerogens undergo loss of hydrogen with increasing pressure and temperature. This typically occurs in geological formations. With the loss of hydrogen and other trace elements such as oxygen, nitrogen, and sulfur and the associated functional groups, the structure and composition of kerogens changes. This leads to aromatization, which allows stacking of molecules into sheets that result in physical characteristics changes. This includes changes in molecular density, reflectance, and coloration. During thermal maturation, kerogen breaks down into bitumen, oil, and gas. The extent of maturation determines the product formed. Lower thermal maturity leads to bitumen or oil formation. Higher thermal maturity leads to gas formation.

At block 402, the $^1$H and $^{13}$C spectra are obtained for the sample tube and the NMR probe at a user-defined set temperature. This is labelled as background signal.

At block 404, the sample source rock which can be crushed or a core plug is placed in the sample tube.

At block 406, the $^1$H and $^{13}$C spectra for the sample source rock are obtained at the same temperature as obtained for the background signal.

At block 408, the background signal is subtracted from the $^1$H and $^{13}$C spectra obtained for the sample source rock.

At block 410, the $^1$H and $^{13}$C spectra are integrated to determine the total hydrogen and carbon content in the source rock sample.

At block 412, The total hydrogen and carbon can be quantified using an external reference sample with a known $^1$H and $^{13}$C spectra. In some implementations, the sample is dimethylpolysiloxane (DMPS). In implementations, DMPS as reference contains $\alpha$ mole of $^1$H and $\beta$ mole of $^{13}$C, which can be obtained from the molecular structure or measured independently.

At block 414, the ratio of hydrogen to carbon can be calculated using the ratio of the integrated $^1$H and $^{13}$C spectra of the source rock sample and the external reference DMPS.

Embodiments of this technology can be implemented manually or automatically. Automatic implementations can be done through machines, hardware, software, firmware, or a program code. A program code to perform the necessary implementations may be stored in a machine readable medium. A processor executes the necessary implementations.

This disclosure provides methods for locating a drilling location based on the accumulation of hydrocarbons. Implementations provide methods to determine source rock maturity, by determining the amount of hydrogen and carbon present in the kerogen of the source rock. Implementations using NMR spectra reveal details about the molecular structure, composition, physical and geochemical characteristics of the kerogen present in the source rock, that are helpful for exploration and drilling activities for commercial oil and gas production.

An embodiment described here provides a method for measuring a subterranean hydrocarbon rock's maturity using a static state high resolution NMR spectroscopic method. In implementations here, a subterranean hydrocarbon rock is drilled for analysis. The subterranean rock includes an organic rich shale rock or mudstone, also known as a source rock. The source rock includes kerogen intertwined with the mineral matrix of the subterranean rock. The bitumen from the source rock is extracted using a solvent. The source rock is placed in an NMR tube and a $^1$H spectrum and $^{13}$C NMR spectra are measured using an NMR probe. The background signal of the NMR probe and the NMR tube are subtracted from the source rock's NMR spectra. The measurement further includes determining the H/C ratio of the kerogen in the source rock sample by integrating the H/C ratio of an external reference sample. In implementations here, the external reference sample includes benzene, hexane, or dimethylpolysiloxane.

An aspect described here provides a system for measuring a subterranean rock's maturity. The system includes an NMR spectrometer which includes an NMR probe, a sample tube in which the subterranean rock is placed, and a user display system to represent the output $^1$H and a $^{13}$C NMR spectra. The subterranean rock includes small core plugs or crushed rocks.

Other implementations are also within the scope of the following claims.

Exemplary Embodiments

Exemplary embodiments include:

1. A method for analyzing maturity of a subterranean hydrocarbon rock, comprising:

obtaining a subterranean hydrocarbon rock sample by drilling through a subterranean zone;

extracting bitumen out of the subterranean hydrocarbon rock sample using a solvent; placing the subterranean hydrocarbon rock sample in a nuclear magnetic resonance (NMR) tube; and measuring a $^1$H spectrum and a $^{13}$C NMR spectrum with a NMR probe using an NMR spectrometer comprising a static state high resolution measurement technique.

2. The method of embodiment 1, wherein the subterranean hydrocarbon rock sample has micro to nano Darcy permeability.

3. The method of embodiment 1 or 2, wherein the subterranean hydrocarbon rock sample comprises a kerogen intertwined within a mineral matrix.

4. The method of embodiment 3, further comprising measuring a hydrogen and carbon (H/C) ratio of the kerogen.

5. The method of embodiment 4, wherein measuring the H/C ratio comprises measuring a degree of aromaticity of the kerogen for the subterranean hydrocarbon rock sample.

6. The method of any one of embodiments 1-5, wherein measuring the $^1$H spectrum and the $^{13}$C NMR spectrum is performed on an intact subterranean hydrocarbon rock sample without further treatment.

7. The method of any one of embodiments 1-6, further comprising measuring the $^1$H spectrum and the $^{13}$C NMR spectrum of the NMR tube and the NMR probe as a background signal, wherein the background signal is subtracted from the $^1$H spectrum and the $^{13}$C NMR spectrum of the subterranean hydrocarbon rock.

8. The method of embodiment 4, further comprising measuring the H/C ratio of kerogen in the subterranean hydrocarbon rock sample by integrating the H/C ratio of an external reference pure organic sample.

9. The method of embodiment 8, wherein the external reference sample is benzene, hexane, or dimethylpolysiloxane.

10. A system for measuring maturity of a subterranean rock, the system comprising:

a nuclear magnetic resonance (NMR) spectrometer comprising an NMR probe, wherein the NMR is configured to operate with a static high resolution technique;

a sample tube, wherein a subterranean rock sample is placed; and a user display system to represent an output NMR spectra comprising a $^1$H spectrum and a $^{13}$C NMR spectrum.

11. The system of embodiment 10, wherein the subterranean rock comprises a kerogen intertwined within a mineral matrix.

12. The system of embodiment 11, wherein a hydrogen/carbon (H/C) ratio of the kerogen is measured by the NMR spectrometer as the $^1$H spectrum and the $^{13}$C NMR spectrum.

13. The system of embodiment 12, wherein the NMR spectrometer comprises a measurement of the $^{1}H$ spectrum and the $^{13}C$ NMR spectrum of the NMR probe and the sample tube as a background signal.

14. The system of any one of embodiments 10-13, wherein the subterranean rock sample comprises small core plugs or crushed rocks.

15. The system of any one of embodiments 10-14, further comprising setting a user defined temperature for the NMR spectrometer.

16. A method of analyzing subterranean rock, the method comprising:

obtaining a subterranean rock sample as a core plug or crushed rock;

placing the subterranean rock sample in a sample tube;

performing a static state high resolution nuclear magnetic resonance (NMR) spectroscopic measurement with a NMR probe to obtain a $^{1}H$ spectrum and a $^{13}C$ NMR spectrum; and displaying the $^{1}H$ spectrum and the $^{13}C$ NMR spectrum on a user display system.

17. The method of embodiment 16, wherein the subterranean rock sample comprises a organic-rich shale or mudrock.

18. The method of embodiment 16 or 17, wherein the subterranean rock sample comprises a kerogen intertwined within a mineral matrix.

19. The method of embodiment 18, wherein a hydrogen/carbon (H/C) ratio of the kerogen is measured by the NMR spectroscopic measurement.

20. The method of embodiment 19, further comprising measuring the H/C ratio of kerogen by integrating the H/C ratio of an external reference sample, wherein the external reference sample is dimethylpolysiloxane.

The invention claimed is:

1. A method for analyzing maturity of a subterranean hydrocarbon rock, comprising:

obtaining a subterranean hydrocarbon rock sample by drilling through a subterranean zone;

extracting bitumen out of the subterranean hydrocarbon rock sample using a solvent;

placing the subterranean hydrocarbon rock sample in a nuclear magnetic resonance (NMR) tube; and measuring a $^{1}H$ spectrum and a $^{13}C$ NMR spectrum with a NMR probe using an NMR spectrometer comprising a static state high resolution measurement technique, wherein measuring the $^{1}H$ spectrum and the $^{13}C$ NMR spectrum is performed on an intact subterranean hydrocarbon rock sample without further treatment.

2. A system for measuring maturity of a subterranean rock, the system comprising:

a nuclear magnetic resonance (NMR) spectrometer comprising an NMR probe, wherein the NMR is configured to operate with a static high resolution technique;

a sample tube, wherein a subterranean rock sample is placed; and a user display system to represent an output NMR spectra comprising a $^{1}H$ spectrum and a $^{13}C$ NMR spectrum, wherein the NMR spectrometer is configured to measure the $^{1}H$ spectrum and $^{13}C$ NMR spectrum of an intact subterranean rock sample without further treatment.

3. A method of analyzing subterranean rock, the method comprising:

obtaining a subterranean rock sample as a core plug or crushed rock;

placing the subterranean rock sample in a sample tube;

performing a static state high resolution nuclear magnetic resonance (NMR) spectroscopic measurement with a NMR probe to obtain a $^{1}H$ spectrum and a $^{13}C$ NMR spectrum, wherein the spectroscopic measurement is performed on an intact subterranean rock sample without further treatment; and displaying the $^{1}H$ spectrum and the $^{13}C$ NMR spectrum on a user display system.

4. The method of claim 1, wherein the subterranean hydrocarbon rock sample has micro to nano Darcy permeability.

5. The method of claim 1, wherein the subterranean hydrocarbon rock sample comprises a kerogen intertwined within a mineral matrix.

6. The method of claim 1, further comprising measuring the $^{1}H$ spectrum and the $^{13}C$ NMR spectrum of the NMR tube and the NMR probe as a background signal, wherein the background signal is subtracted from the $^{1}H$ spectrum and the $^{13}C$ NMR spectrum of the subterranean hydrocarbon rock.

7. The system of claim 2, wherein the subterranean rock comprises a kerogen intertwined within a mineral matrix.

8. The system of claim 2, wherein the subterranean rock sample comprises small core plugs or crushed rocks.

9. The system of claim 2, further comprising setting a user defined temperature for the NMR spectrometer.

10. The method of claim 3, wherein the subterranean rock sample comprises an organic-rich shale or mudrock.

11. The method of claim 3, wherein the subterranean rock sample comprises a kerogen intertwined within a mineral matrix.

12. The method of claim 5, further comprising measuring a hydrogen and carbon (H/C) ratio of the kerogen.

13. The system of claim 7, wherein a hydrogen/carbon (H/C) ratio of the kerogen is measured by the NMR spectrometer as the $^{1}H$ spectrum and the $^{13}C$ NMR spectrum.

14. The method of claim 11, wherein a hydrogen/carbon (H/C) ratio of the kerogen is measured by the NMR spectroscopic measurement.

15. The method of claim 12, wherein measuring the H/C ratio comprises measuring a degree of aromaticity of the kerogen for the subterranean hydrocarbon rock sample.

16. The method of claim 12, further comprising measuring the H/C ratio of kerogen in the subterranean hydrocarbon rock sample by integrating the H/C ratio of an external reference pure organic sample.

17. The system of claim 13, wherein the NMR spectrometer comprises a measurement of the $^{1}H$ spectrum and the $^{13}C$ NMR spectrum of the NMR probe and the sample tube as a background signal.

18. The method of claim 14, further comprising measuring the H/C ratio of kerogen by integrating the H/C ratio of an external reference sample, wherein the external reference sample is dimethylpolysiloxane.

19. The method of claim 16, wherein the external reference sample is benzene, hexane, or dimethylpolysiloxane.

* * * * *